United States Patent [19]

Wick

[11] 4,138,586

[45] Feb. 6, 1979

[54] PROCESS FOR ALKANOYL PROPIONATES

[75] Inventor: Alexander E. Wick, Riehen, Switzerland

[73] Assignee: Hoffmann-La Roche Inc., Nutley, N.J.

[21] Appl. No.: 622,289

[22] Filed: Oct. 14, 1975

[51] Int. Cl.$^2$ .................... C07C 67/30; C07C 69/67
[52] U.S. Cl. .................... 560/174; 260/410.9 R; 260/465.1
[58] Field of Search .................... 260/483, 410.9 R; 560/174

[56] References Cited

U.S. PATENT DOCUMENTS 3,492,337  1/1970  Watson et al. .................... 260/483

OTHER PUBLICATIONS

McMurry et al., J. Org. Chem., vol. 39, #2, 1974, pp. 259–260.

Primary Examiner—Vivian Garner
Attorney, Agent, or Firm—Jon S. Saxe; Bernard S. Leon; George M. Gould

[57] ABSTRACT

The present disclosure is concerned with a process for the preparation of alkanoyl propionates and alkanoyl propionitriles from γ-nitro-alkanecarboxylic acid esters and alkyl-γ-nitro-propionitriles.

4 Claims, No Drawings

PROCESS FOR ALKANOYL PROPIONATES

BACKGROUND OF THE INVENTION

It is known that 4-nitropimelic acid esters can be converted into 4-oxo-pimelic acid esters by means of the Nef reaction. However, in the application of this reaction to the manufacture of alkanoyl propionates on a technical scale, a series of disadvantages are encountered. Thus, the Nef reaction requires a precise check on the specific range of the reaction temperature. Furthermore, there are formed considerable amounts of salt, the removal of which gives rise to problems. On the other hand, the ozonolysis following the nitronate formation, which is described in J. Org. Chem. 39, 260 (1974), stipulates a working at a low temperature and the use of sodium methoxide (i.e., working with the exclusion of moisture).

DESCRIPTION OF THE INVENTION

Surprisingly, it has now been found in accordance with the present invention that the transformation of the nitro group of Y-nitro-alkanecarboxylic acid esters and corresponding nitriles into the oxo group can be carried out under simple and technically advantageous conditions, namely using an alkali metal hydroxide in an alkanol as the base. It is then possible to carry out the ozonization of the nitronate at 0° C.

The present invention is based on the foregoing finding and accordingly comprises treating a compound of the general formula

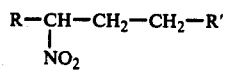

wherein R is lower alkyl, preferably ethyl or propyl; and R' is esterified carboxyl or nitrilo with an alkali metal hydroxide in an alkanol, ozonizing the product obtained and working up the ozonization product to give a compound of the general formula

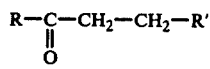

wherein R and R' have the significance given earlier.

Examples of esterified carboxyl groups denoted by R' are lower alkoxycarbonyl groups such as the methoxycarbonyl and ethoxycarbonyl groups. As the alkanol there is conveniently used the alkanol corresponding to the ester group. Preferred alkali metal hydroxides are sodium hydroxide and potassium hydroxide. The ozonolysis can be carried out in a manner known per se; for example, by introducing ozone or an ozone/oxygen mixture which is generated in a commercial ozonizer. As mentioned earlier, the ozonolysis can be carried out at about 0° C. The working up of the ozonization product is preferably carried out reductively; for example, by treatment with sodium hydrogen sulfite, sodium sulfite, dimethyl sulfide or zinc/glacial acetic acid. However, the working up can also be carried out oxidatively; for example, by means of hydrogen peroxide/-formic acid or silver oxide.

The nitriles of formula II can be converted according to known methods into carboxylic acid esters, for example, by acidic or basis hydrolysis and esterification of the resulting carboxyl group or via iminoethers.

The carboxylic acid esters of formula II are intermediates in the synthesis of steroids (see, for example, U.S. Pat. No. 3,852,331). They are used at a relatively early stage of the synthesis and, for this reason, it is especially desirable that they should be accessible by an economic process. The process provided by this invention now offers an especially economic access to these esters since it is technically unproblematic to operate, proceeds in higher yields and uses cheap starting materials.

The starting materials of formula I are known or can be prepared according to methods known per se; for example, by the base-catalyzed addition of nitroalkanes to acrylic acid esters.

The following examples illustrate the present invention.

EXAMPLE 1

In a 4.5 liter four-necked sulfonation flask provided with a mechanical stirring apparatus, a thermometer, a gas-inlet tube bent in the direction of stirring and a ventilation head, 189.2 g. (1.0 mol) of 4-nitrohexanoic acid ethyl ester are treated at room temperature with a solution of 44 g. (1.1 mol) of sodium hydroxide in 1.6 liters of absolute ethanol and cooled to 0° C. in an ice bath. At this temperature during 25 hours with vigorous stirring, an ozone/oxygen stream is introduced into the initially clear, orange-red solution. After completion of the ozonization, the mixture is flushed with nitrogen for 10 minutes and filtered from the colorless precipitate through a Celite bed into a flask which contains a solution of 156 g. (1.5 mol) of sodium bisulfite in 350 ml. of water. The mixture is re-washed with 200 ml. of ethanol, the colorless to light yellow mixture stirred for 30 minutes at room temperature and again filtered through a suction filter charged with Celite and re-washed with 200 ml. of ethanol. 1800 ml. of solvent are distilled off via a 20 cm Vigreux column at normal pressure and a bath temperature of 110° C. and the two-phase residue is separated in a separating funnel. To the upper phase are added 100 ml. of water and both of the phases are extracted successively, first with 200 ml. of chloroform and then a further three times with 100 ml. of chloroform each time (total 300 ml.). The combined organic phases are dried over 150 g. of sodium sulfate, the solvent is distilled off at normal pressure through a 20 cm Vigreux column and the residue distilled in the same apparatus under a high vacuum. There are obtained 135 g. (85.8%) of colorless 4-oxohexanoic acid ethyl ester; boiling point 63–65°/0.1 mm; gas-chromatographic purity > 98%.

EXAMPLE 2

The process described in Example 1 was repeated with varying reaction conditions. These conditions and the results obtained are compiled in the following Table:

Table

| Amount of nitro-hexanoic acid used (mol) | NaOH (mol) | Ethanol (ml) | Reaction time | Reduction agent | Working up with solvent | Yield % |
|---|---|---|---|---|---|---|
| 0.20 | 0.22 | 350 | 5h 25 min | NaHSO₃ | Ether | 82.0 |
| 0.20 | 0.22 | 350 | 5h 15 min | NaHSO₃ | CHCl₃ | 87.7 |
| 1.0 | 1.10 | 1600 | 25h | NaHSO₃ | CHCl₃ | 85.8 |

EXAMPLE 3

In a manner analogous to that described in Example 1, from 0.40 mol of 4-nitroheptanoic acid methyl ester and 0.44 mol of sodium hydroxide in 640 ml. of ethanol there was obtained, after carrying out the ozonization for 10.5 hours and after working up with sodium hydrogen sulfite, 4-oxoheptanoic acid methyl ester in 80.9% yield.

EXAMPLE 4

In a manner analogous to that described in Example 1, from 4-nitrocapronitrile there was obtained 4-oxocapronitrile in 80% yield.

I claim:

1. A process for the preparation of compounds of the formula

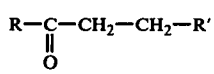

wherein R is lower alkyl and R' is lower alkoxycarbonyl which process comprises treating a compound of the formula

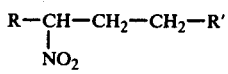

wherein R and R' are as above with an alkali metal hydroxide in an alkanol, ozonizing the product obtained at a temperature of about 0° C. and working up the ozonization product by reductive treatment with an agent selected from sodium hydrogen sulfite, sodium sulfite, dimethyl sulfide or zinc/glacial acetic acid or oxidative treatment with an agent selected from hydrogen peroxide/formic acid or silver oxide.

2. A process according to claim 1 wherein there is used a compound in which R is ethyl or propyl.

3. A process according to claim 1 wherein the ozonization product is worked up reductively.

4. A process according to claim 3 wherein the ozonization product is treated with a sodium hydrogen sulfite solution.